United States Patent [19]

Gilmore et al.

[11] Patent Number: 4,775,419

[45] Date of Patent: Oct. 4, 1988

[54] METAL AMINE COMPLEXES FOR IMPROVING THE BOND STRENGTH PROPERTIES OF ASPHALT

[75] Inventors: Dennis W. Gilmore, Fairfield; Larry M. Girdler, Norwood; Thomas G. Kugele, Cincinnati, all of Ohio

[73] Assignee: Morton Thiokol, Inc., Chicago, Ill.

[21] Appl. No.: 522,952

[22] Filed: Aug. 12, 1983

[51] Int. Cl.$^4$ ............................................. C08L 95/00
[52] U.S. Cl. .............................. 106/281.1; 106/273.1
[58] Field of Search ................. 106/273, 273 N, 277, 106/281 N; 252/311.5; 260/429.3-429.9

[56] References Cited

U.S. PATENT DOCUMENTS

| | | | |
|---|---|---|---|
| 3,046,149 | 7/1962 | Moore et al. | 106/273 |
| 3,093,595 | 6/1963 | Levy et al. | 106/277 |
| 3,259,512 | 7/1966 | Dickson et al. | 106/273 |
| 3,928,061 | 12/1975 | Hellsten et al. | 106/277 |
| 3,933,710 | 1/1976 | Fukushi et al. | 524/61 |
| 4,008,096 | 2/1977 | Knapp | 106/277 |
| 4,142,903 | 3/1979 | Antonelli; Sr. | 106/273 N |
| 4,349,590 | 9/1982 | Bolen et al. | 106/277 |
| 4,370,170 | 1/1983 | Tolonen et al. | 106/277 |
| 4,430,127 | 2/1984 | Dalter et al. | 106/277 |

OTHER PUBLICATIONS

Derwent Abstract Accession number 79-47979B/26, Japanese Patent No. J54062202, May 18, 1979.
Chemical Abstract, vol. 84, No. 14, 94684K, Japanese Patent No. JP50/110419, Aug. 30, 1975.
Derwent Abstract No. CA82(20):127415n, Saiuchi et al., "Emulsifier for an Asphalt," Jun. 12, 1974.
Lee, et al., *Handbook of Epoxy Resins*, McGraw-Hill Book Co. (New York: 1982), pp. 7–26.

Primary Examiner—Amelia Burgess Yarbrough
Attorney, Agent, or Firm—George Wheeler; Gerald K. White

[57] ABSTRACT

Metal amine complexes are formed from amines adhering to the general formulas

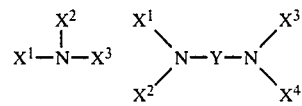

by reaction with various metal salts. Prior to reaction with various metal salts, the above amines may first be reacted with a formaldehyde source or with a formaldehyde source followed by an epoxide or with an epoxide or with an epoxide followed by a formaldehyde source. The resultant metal amine complexes are then employed in asphalt compositions in order to increase the overall strength of such compositions.

42 Claims, No Drawings

METAL AMINE COMPLEXES FOR IMPROVING THE BOND STRENGTH PROPERTIES OF ASPHALT

CROSS REFERENCE TO RELATED APPLICATION

This application generally relates to the subject matter disclosed in co-pending application of Dennis W. Gilmore and Thomas G. Kugele entitled "Asphalt-Adhesion Improving Additives Prepared by Formaldehyde Condensation With Polyamines", which has been filed on the same date as the present application and is hereby incorporated by reference.

BACKGROUND OF THE INVENTION

The present invention relates to the production of asphalt compositions, such as those used in paving and roofing applications, which have increased tensile strength and increased adhesion between the asphalt and a filler, e.g. mineral aggregate or glass fiber or a glass fiber mesh.

Asphalt may be generally described as a dark-brown to black cementitious material, solid or semi-solid in consistency, in which the primary constituents are a mixture of paraffinic and aromatic hydrocarbons and heterocyclic compounds containing sulfur, nitrogen and oxygen. As discussed in *The Asphalt Handbook* (The Asphalt Institute Manual, Series No. 4, 1965 ed.), incorporated herein by reference, various grades of asphalt may be produced by selecting different processing conditions. In this regard two basic types of solid asphalt, asphalt cement and air-blown asphalt, and two basic types of liquid asphalt, cutback asphalt and emulsified asphalt, are utilized commercially. Asphalt cement is defined as asphalt which has been refined to meet paving and industrial specifications; cutback asphalt is asphalt cement which has been liquified by blending with petroleum solvents; and asphalt emulsions are prepared such that the asphalt is emulsified in the inner phase (an oil-in-water type emulsion). The emulsion can also be of the water-in-oil type in which water constitutes the inner phase (see Hellsten et al, "Asphalt Compositions Having Improved Adhesion to Aggregate", U.S. Pat. No. 3,928,061).

The particle size of mineral aggregate used in an asphalt composition may vary over a wide range, such as from $2 \times 10^{-5}$ to $6 \times 10^{-2}$ meters in diameter, or the aggregate may be of a fairly uniform size. Mineral aggregates employed in asphalt compositions also range in character from hydrophilic to hydrophobic. It has long been known that mineral aggregates have a greater attraction for water than for oil or asphalt. In general, it can be said that siliceous and acidic minerals such as sands and gravels tend to be very hydrophilic whereas calcareous and alkaline materials such as limestone tend to be slightly hydrophilic. It is difficult, therefore, to obtain and maintain a satisfactory asphalt coating on the mineral aggregate particles when water is present. One example of an asphalt composition is the combination of asphalt cement with a size-graded mineral aggregate. This combination is referred to as asphalt concrete and is used in road paving applications. A poor asphalt coating on the mineral aggregate leads to breakup of the asphalt concrete and commonly results in potholes and flaking pavements.

One common method of pavement construction is to remove water from the aggregate by forced evaporation prior to coating with asphalt cement. In practice, this requires a certain amount of aggregate drying time which consumes energy and may result in a lengthened construction period. If weather conditions are unfavorable, such as during periods of rainfall or high humidity, road construction may be severely hindered if not halted. Even if the water is removed and the asphalt successfully deposited onto the aggregate, the asphalt coating may ultimately be degraded by the action of groundwater or rainfall.

A successful method of increasing pavement life has been to add one or more antistripping additives to the asphalt composition. Such additives increase the hydrophobicity of the aggregate, thereby strengthening and preserving the asphalt-aggregate bond. While antistripping additives have been found to be successful in certain paving and roofing applications, conventional asphalt compositions employing such additives are still limited in that the strength of the asphalt-aggregate bond is often not sufficient to resist damage from prolonged conditions of stress and wear.

Accordingly, it is an object of the present invention to provide for an asphalt composition employing additives which will improve the overall bond strength properties of said compositions. It is a further object of the present invention to provide for an asphalt additive comprised of certain metal amine complexes which will significantly increase the overall tensile strength and durability to harmful environmental conditions of an asphalt composition by virtue of an improved asphalt-aggregate bond.

These and other objects of the invention will become apparent from the following detailed description and appended claims.

SUMMARY OF THE INVENTION

It has now been found that the foregoing objects may be accomplished by the use of metal amine complexes which result in a surprisingly high level of adhesion between the mineral aggregate or glass fibers or glass fiber mesh and asphalt, and thus an improved overall composition tensile strength and greater durability to harmful environmental conditions.

There can be used, for example, 0.2 to 2.0 (preferably 0.3 to 1.0) parts of metal amine complex per 100 parts by weight of asphalt.

In particular, the present invention relates to the formation of metal salts complexed with amines or polyamines and the use of such metal amine complexes in asphalt compositions. The amines and polyamines which form starting materials for the invention are taken from the following general formulae:

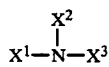  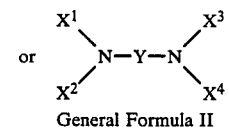

General Formula I    General Formula II where: $X^1$, $X^2$, $X^3$, $X^4$ are the same or different and can be

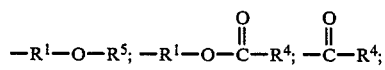

-continued

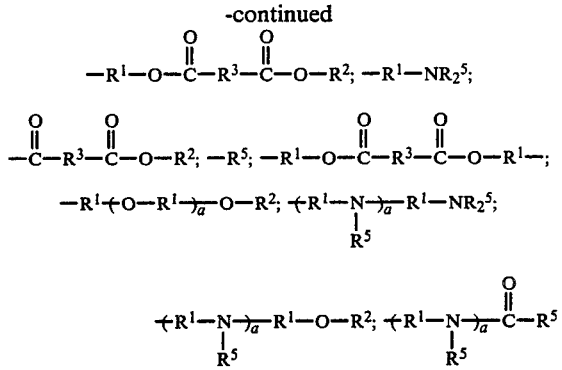

and hydrogen or forms a 5 or 6-membered ring containing at least one nitrogen atom and carbon atoms with or without oxygen atoms and can be substituted by $R^5$. Illustative ring systems include morpholine, piperazine, piperidine and imidazoline.

In all of the amine systems mentioned above at least one nitrogen must not be tertiary (i.e. at least one X or one $R^5$ must be hydrogen).

Y is selected from the group consisting of

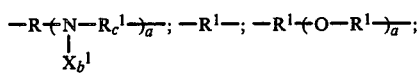

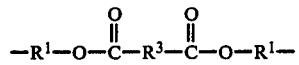

or forms a 6-membered ring containing two nitrogens (such a structure then requires only one X to be attached to the nitrogen).

R is alkylene up to six carbon atoms, e.g. methylene, ethylene, hexamethylene or cyclohexamethylene; and can form a 6-membered ring with two nitrogens.

$R^1$ is alkylene, e.g. methylene, ethylene, hexamethylene or even up to eicosanylene, cycloalkylene, e.g. cyclohexamethylene; arylene, e.g. phenylene or naphthylene; hydroxy, ester or hydrocarbyl-substituted alkylene, cycloalkylene and arylene.

$R^2$ is alkyl, e.g. methyl, ethyl, butyl, eicosanyl; cycloalkyl, e.g. cyclohexyl; aryl, e.g. phenyl or naphthyl; alkaryl, e.g. tolyl; aralkyl, e.g. benzyl; or the previous substituted by hydroxy or ester. $R^2$ can also be hydrogen.

$R^3$ is alkylene; cycloalkylene; arylene or the previous substituted by hydrocarbyl, hydroxy, ester; —CH=CH—. Illustative groupings for $R^1$ apply equally here.

$R^4$ is alkenyl, e.g. propenyl, hexenyl, octadecenyl; alkyl; aryl; alkaryl; aralkyl; cycloalkyl; or the previous substituted by hydroxy or ester;

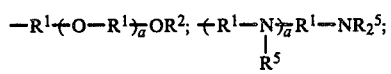

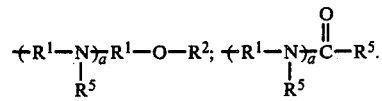

Illustrative groupings for $R^2$ apply equally here.

$R^5$ is hydrogen; alkenyl; alkyl; cycloalkyl; aryl; alkaryl; aralkyl; or the previous substituted by hydroxy, ester, alkyl imidazoline or alkenyl imidazoline; alkyl imidazoline or alkenyl imidazoline;

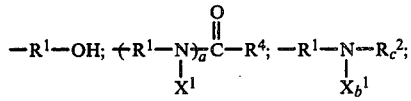

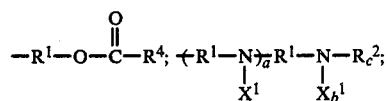

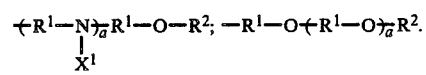

a is 0 to 6; b is 0, 1, 2,; c is 0, 1, 2. With the proviso that when a compound of General Formula I contains at least two nitrogen atoms this compound is not within General Formula II.

The following chart illustrates examples of amines within General Formula I which are useful in obtaining the end products according to the invention.

| Example No. | $X^1$ | $X^2$ | $X^3$ |
|---|---|---|---|
| 1. | $CH_3(CH_2)_{10}CH_2-$ | $-CH_2CH_2OH$ | $-H$ |
| 2. | $CH_3(CH_2)_{12}CH_2-O(CH_2-\underset{H}{\overset{CH_3}{\underset{|}{C}}}-O)_2CH_2-\underset{H}{\overset{CH_3}{\underset{|}{C}}}$ | $-H$ | $-H$ |
| 3. | $CH_3-$ | $CH_3-$ | $-H$ |
| 4. | | $O\underset{CH_2CH_2}{\overset{CH_2CH_2}{\diagup\diagdown}}$ | $-H$ |
| 5. | phenyl-$CH_2-$ | $CH_3-$ | $-H$ |

-continued

| Example No. | $X^1$ | $X^2$ | $X^3$ |
|---|---|---|---|
| 6. | [cyclohexane ring with S, methyl substituent] | —H, | —H |
| 7. | [phenyl-CH(OH)-CH$_2$-O-CH$_2$CH$_2$—] | —H, | —H |
| 8. | O=C-O-(CH$_2$)$_3$CH$_2$— attached to phenyl with —C(CH$_3$)$_3$ para substituent | —H, | —H |
| 9. |  | [piperidine-like ring: CH$_2$/CH$_2$CH$_2$/CH$_2$CH$_2$] | —H |
| 10. | [phenyl-methyl] | [phenyl-methyl] | —H |
| 11. |  | CH$_3$-C(=N-CH$_2$)-CH$_2$ (cyclic imine) | —H |
| 12. | CH$_3$CH$_2$O-C(=O)-CH=CH-C(=O)-O-(CH$_2$)$_3$CH$_2$— | —H, | —H |
| 13. |  | CH$_3$-(CH$_2$)$_7$-CH=CH-(CH$_2$)$_7$-C(=N-CH$_2$)-CH$_2$ | —H |
| 14. | CH$_3$-CH(OH)-CH$_2$—, | CH$_3$-CH(OH)-CH$_2$—, | —H |
| 15. | [cyclohexane with S, -O-C(=O)-CH$_3$ substituent] | —H, | —H |
| 16. | 4-(tert-butyl)phenyl-O-(CH$_2$CH$_2$O)$_2$-CH$_2$CH$_2$—, | 4-(tert-butyl)phenyl-O-(CH$_2$CH$_2$O)$_2$-CH$_2$CH$_2$—, | —H |
| 17. | HO(CH$_2$)$_3$CH$_2$—, | HO(CH$_2$)$_3$CH$_2$—, | —H |

The following chart illustrates examples of amines within the General Formula II which are useful in obtaining the end products according to the invention.

| Example No. | $X^1$ | $X^2$ | $X^3$ | $X^4$ | Y |
|---|---|---|---|---|---|
| 1. | —H, | —H, | —H, | —H, | ![para-phenylene ring] |
| 2. | ![PhCH(OH)CH₂—] | —H, | —H, | —H, | —CH₂CH₂—O—CH₂CH₂— |
| 3. | CH₃—, | —H, | CH₃—, | —H, | ![2-methylphenyl (tolyl)] CH₃ |
| 4. | —H, | —H, | —H, | —H, | —CH₂CH₂CH₂—N—CH₂CH₂— <br> \|  <br> CH₂(CH₂)₁₆CH₃ |
| 5. | —CH₂CH₂OH, | —H, | —CH₂CH₂OH, | —H, | —CH₂CH₂CH₂—N—CH₂CH₂— <br> \| <br> CH₂CH₃ |
| 6. | —CH₂CH₂OH, | —CH₂CH₂OH, | —CH₂CH₂OH, | —H, | O        O <br> ‖         ‖ <br> —CH₂CH₂O—C—(CH₂)₄—C— |
| 7. | —H, | —H, | —H, | —H, | CH₃ <br> \| <br> —(CH₂)₆—N—CH₂CH₂O—C=O <br>                         \| <br>                        (CH₂)₄ <br>                         \| <br> —(CH₂)₆—N—CH₂CH₂O—C=O <br> \| <br> CH₃ |
| 8. | CH₃ <br> \| <br> —CH₂—C—OH, <br> \| <br> H | —H, | CH₃ <br> \| <br> —CH₂—C—OH, <br> \| <br> H | —H, | CH₃ <br> \| <br> —(CH₂)₆—N—CH₂CH₂O—C=O <br>                         \| <br>                        (CH₂)₄ <br>                         \| <br> —(CH₂)₆—N—CH₂CH₂O—C=O <br> \| <br> CH₃ |
| 9. | —CH₂CH₂CH₂NH₂ | —H, | —CH₂CH₂CH₂NH₂, | —H, | —(CH₂)₆— |

-continued

| Example No. | X¹ | X² | X³ | X⁴ | X⁵ |
|---|---|---|---|---|---|
| 10. | $-CH_2CH_2OCH_2CH_3$, | $-H$, | $-CH_2CH_2OCH_2CH_3$, | $-H$, | $-(CH_2)_6-\underset{H}{N}-(CH_2)_6-$ |
| 11. | $\underset{CH_3}{\overset{CH_3}{N}}-CH_2-(CH_2)_4-CH_2-$, | $-H$, | $\underset{CH_3}{\overset{CH_3}{N}}-CH_2-(CH_2)_4-CH_2-$, | $-H$, | $-CH_2CH_2-$ |
| 12. | $CH_3CH_2OCH_2CH_2-\underset{H}{N}-(CH_2)_5-CH_2-$, | $-H$, | $-H$, | $-H$, | $-(CH_2)_4-$ |
| 13. | $-CH_2CH_2OH$, | — | $-H$, | — | cyclohexane-1,2-diyl (via $-CH_2CH_2-/-CH_2CH_2-$) |
| 14. | $\text{PhCH}_2-$, | — | $-H$, | — | cyclohexane-1,2-diyl |
| 15. | $CH_3O-\overset{O}{\underset{\parallel}{C}}-CH=CH-\overset{O}{\underset{\parallel}{C}}-$, | — | $-H$, | — | cyclohexane-1,2-diyl |
| 16. | $CH_3\overset{O}{\underset{\parallel}{C}}-$, | $-H$, | $-H$, | $-H$, | naphthalene-1,8-diyl |
| 17. | $\text{Ph}-\overset{O}{\underset{\parallel}{C}}-O-CH_2CH_2-$, | $-H$, | $-CH_2CH_3$, | $-CH_2CH_3$, | $-(CH_2)_3-$ |
| 18. | $CH_3-(CH_2)_{10}-CH_2-O-\overset{O}{\underset{\parallel}{C}}-CH_2-\overset{O}{\underset{\parallel}{C}}-O-CH_2CH_2-$, | $-H$, | $-H$, | $-H$, | $-CH_2CH_2-O-CH_2CH_2-$ |

-continued

| # | | | | |
|---|---|---|---|---|
| 19. | $CH_3-\overset{O}{\overset{\|}{C}}-\overset{H}{\overset{\|}{N}}-CH_2CH_2CH_2-$, | −H, | −CH$_2$CH$_2$CH$_2$NH$_2$, | $-(CH_2)_6-$ |
| 20. | $\underset{\underset{O}{\underset{\|}{CH_2CH_2}}}{\overset{CH_2CH_2}{\overset{\|}{N}}}-CH_2CH_2-\overset{H}{\overset{\|}{N}}CH_2CH_2-$, | −H, | $\underset{\underset{O}{\underset{\|}{CH_2CH_2}}}{\overset{CH_2CH_2}{\overset{\|}{N}}}-CH_2CH_2-\overset{H}{\overset{\|}{N}}CH_2CH_2-$, | $-(CH_2)_6-$ |
| 21. | $\underset{\underset{O}{\underset{\|}{CH_2CH_2}}}{\overset{CH_2CH_2}{\overset{\|}{N}}}-CH_2CH_2-O-\overset{O}{\overset{\|}{C}}-CH_2-\overset{O}{\overset{\|}{C}}-OCH_2CH_2-$, | −H, | −H, | $-(CH_2)_2-$ |
| 22. | HOCH$_2$CH$_2-$, | −H, | HOCH$_2$CH$_2-$, | $-CH_2CH_2-O-\overset{O}{\overset{\|}{C}}-CH=CH-\overset{O}{\overset{\|}{C}}-O-\overset{CH_2}{\overset{\|}{CH_2}}-$ |
| 23. | $\underset{\underset{H-N}{\underset{\|}{CH_2CH_2}}}{\overset{CH_2CH_2}{\overset{\|}{}}}$, | CH$_3-$, | CH$_3-$, | $-(CH_2)_3-$ |
| 24. | $\underset{\underset{O}{\underset{\|}{CH_2CH_2}}}{\overset{CH_2CH_2}{\overset{\|}{}}}$, | CH$_3-$, | CH$_3-$, | $-(CH_2)_3-$ |

The compounds described by General Formulas I or II, including any mixtures thereof, can be reacted with up to 50 weight percent formaldehyde or a conventional formaldehyde source, e.g. paraformaldehyde, trioxane or hexamethylenetetramine, to produce various intermediate formaldehyde condensation products. An example of one such reaction and the resultant intermediate products can be illustrated as follows:

Illustration 1

$H_2N(CH_2)_6NH_2 + CH_2O \longrightarrow H_2N(CH_2)_6NHCH_2OH,$ $[H_2N(CH_2)_6NH]_2CH_2, H_2N(CH_2)_6NH(CH_2O)_3H, HOCH_2NH(CH_2)_6NHCH_2OH, HOCH_2NH(CH_2)_6N(CH_2OH)_2,$ $[H(OCH_2)_2]_2N(CH_2)_6NHCH_2OH, HOCH_2NH(CH_2)_6NHCH_2NH(CH_2)_6NHCH_2OH,$ $HOCH_2NH(CH_2)_6NH[CH_2NH(CH_2)_6NH]_6CH_2NH(CH_2)_6NHCH_2OH,$ and the like.

The intermediate compounds (shown by example only in Illustration 1) may be further reacted with ethylene oxide, ethylene oxide containing an alkyl, cycloalkyl or aryl substituent or cyclohexylene oxide to yield a third group of amines useful in forming the end products according to the invention. An example of one such reaction can be illustrated as follows:

Illustration 2

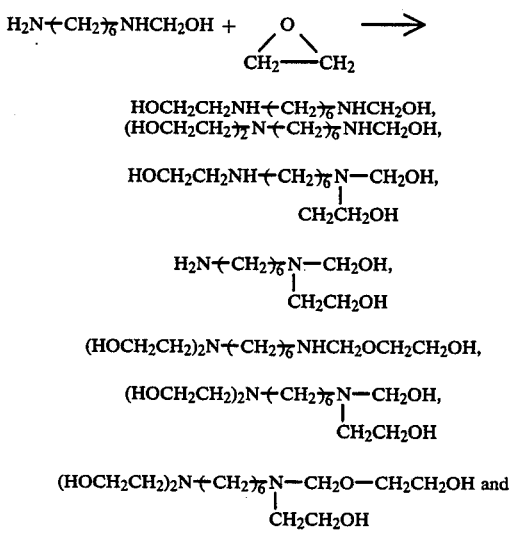

like compounds.

The methods for preparing the foregoing amine compounds are well known in the chemical literature and include methathesis, condensation, esterification, amidization, epoxidation and transesterification. Thus, as shown by Examples A and B below, it should be clear to those skilled in the art that the end product(s) obtained depend on the stoichiometry, reaction temperature (0°–200° C.), order of reagent addition, type of catalyst used (if any) and time of addition and reaction length.

EXAMPLE A 103 grams (1.0 mole) of diethylenetriamine was placed into a three-necked flask and heated to 100° C. 18 grams (0.6 mole) of paraformaldehyde was then added over a one-hour period while slowly increasing the temperature of the mixture to 150° C. The temperature was then held at 150° C. for one hour producing a dark, viscous, tacky fluid weighing 109.5 grams and having a composition similar to that described in Illustration 1 above.

EXAMPLE B 109.5 grams (1.0 mole) of the reaction product of Example A was placed into a three-necked flask and heated to 100° C. 44 grams (1.0 mole) of ethylene oxide was then slowly added and the mixture maintained at 100° for 90 minutes. The vessel pressure was then reduced to 25 mm Hg to remove any volatile material. The reaction mixture residue weighed 153 grams and was a dark, viscous, tacky liquid having a composition similar to that described in Illustration 2 above. As can be seen from Example B and Illustration 2 this procedure does not form polyalkyleneoxide groups.

The intermediate amines described by the foregoing Illustrations and Examples may then be reacted with various metal salts to produce the compounds according to the present invention. Such metals of the metal salts are taken from groups IIA, IVB, VIIB, VIII, IB, IIB, IIIA or IVA of the periodic chart of elements or chromium, or are salts of mono- or dialkyl tin or mono-, di- or trialkyl silicon. Examples of such metals are copper, tin, alkyltin, manganese, lead, aluminum, silicon, alkylsilicon, iron, titanium, magnesium, zinc, calcium, cobalt, nickel, chromium and zirconium and exist in their normal oxidation states as, for example, $Cu^{+1}$ and $Cu^{+2}$. In this regard, the preferred metals include copper, silicon, tin and manganese. The anions include Cl, Br, oxide, hydroxy, sulfate, carboxylates

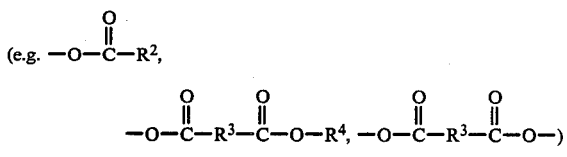

and tri or penta-valent phosphorus derivatives which contain at least one P-OH linkage. Illustrative metal salts include cuprous chloride, cupric chloride, cupric bromide, cupric sulfate, cupric oxide, cupric hydroxide, cupric acetate, cupric carbonate, cupric succinate, cupric formate, cupric maleate, cupric bis(methylmaleate), cupric phosphate, cupric phosphite, cupric methanephosphonate, cupric benzene phosphonate, cupric benzene phosphonite, stannic chloride, stannous chloride, stannous bromide, stannous oxide, methyltin trichloride, dimethyltin dichloride, butyltin trichloride, dibutyltin dichloride, octyltin trichloride dioctyltin dichloride, monobutyltin oxide, dibutyltin oxide, monomethyltin oxide, dimethyltin oxide, stannic tetrakis(2-ethylhexanoate), dimethylsilicon dichloride, trimethylsilicon chloride. The same salts and types of salts can be used with any of the other metals. Likewise, there can be employed metal salts of any of the above mentioned metals with any of the anions mentioned in the following tables and examples. It should be noted that mixtures of metals and mixtures of anions can be used. It should be noted that in the case of silicon and tin tetrahalides are preferably avoided. Exemplary preparations of the metal amine complexes according to the invention are set forth in Examples C and D below.

EXAMPLE C 153 gms. (1.0 mole) of the reaction product obtained in Example B was placed into a three-necked flask and heated to 80° C. Over a one-hour period, 135 gms. (1.0 mole) of cupric chloride dissolved in 1200 gms isopropanol was added to the mixture. The material was refluxed for one hour and then the solvent was removed under reduced pressure. The product produced was a thick, tacky liquid weighing 288 gms.

EXAMPLE D 153 gms. (1.0 mole) of the product obtained in Example B was placed into a three-necked flask and heated to 80° C. Over a one-hour period, 245 gms. (1.0 mole) of manganese acetate tetrahydrate dissolved in 1200 gms. of isopropanol was added to the mixture, which was then distilled at atmospheric pressure until 800 ml of end product material was accumulated. The pressure was then reduced to 25 mm Hg and the mixture was heated to 100° C. The resultant product was a dark viscous, tacky liquid weighing 322 gms.

The theoretical structures of Examples C and D are believed to include the following compounds, as well as others, produced in accordance with the foregoing reaction sequences.

For Example C:

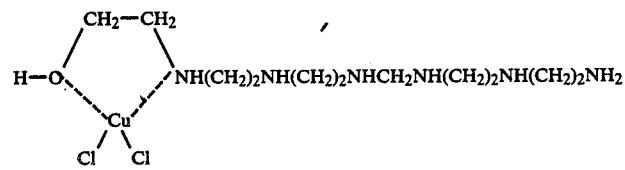

For Example D:

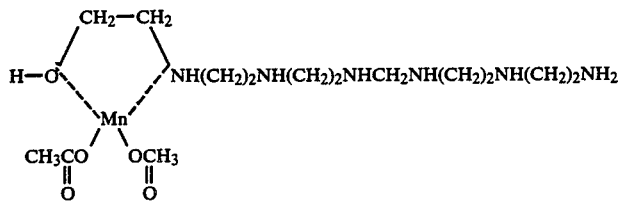

Consistent with the above description, various exemplary amine compounds were reacted with either a formaldehyde source or an epoxide as set forth in Table I below to form intermediate amine products useful in producing the metal amine complexes according to the invention.

TABLE I

| Compound No. | Amine Reactant | Other Reactant | Mole Ratio[1] |
|---|---|---|---|
| 1 | Crude Bis-hexamethylenetriamine (Source A) | — | — |
| 2 | Crude Bis-hexamethylenetriamine (Source B) | ethylene oxide | 1.0:2 |

TABLE I-continued

| Compound No. | Amine Reactant | Other Reactant | Mole Ratio[1] |
|---|---|---|---|
| 3 | Pure Bis-hexamethylenetriamine | paraformaldehyde | 1.6:1 |
| 4 | Compound 3 | propylene oxide | 1.0:1 |
| 5 | Hexamethylenediamine | ethylene oxide | 1.0:1 |
| 6 | Compound 5 | paraformaldehyde | 1.6:1 |
| 7 | Triethylenetetraamine | — | — |
| 8 | N—hydroxyethyl piperazine | — | — |
| 9 | Diethylenetriamine | ethylene oxide | 1.0:1 |
| 10 | Compound 9 | paraformaldehyde | 1.0:1 |
| 11 | Diethylenetriamine | paraformaldehyde | 1.2:1 |
| 12 | Compound 11 | styrene oxide | 1.4:1 |
| 13 | n-octylamine | ethylene oxide | 1.0:1 |
| 14 | $\begin{array}{c}\phantom{CH_3-}N-CH_2\\\phantom{CH_3-}\parallel\phantom{-CH_2}\\ CH_3-C\phantom{-CH_2}\\\phantom{CH_3-}\mid\phantom{-CH_2}\\\phantom{CH_3-}N-CH_2\\\phantom{CH_3-CH}\diagdown\\\phantom{CH_3-CHCH}CH_2CH_2NH_2\end{array}$ | propylene oxide | 1.0:1 |

NOTES:
[1]Refers to mole ratio of amine to co-reactant.

Thereafter, the intermediate compositions obtained from the reaction components set forth in Table I were combined with exemplary metal salts according to the mole ratios set forth in Table II below.

TABLE II

| Compound | From Table 1 | Amine Reactant Metal Salt Reactant | Mole Ratio[1] |
|---|---|---|---|
| 1 | 1 | cupric chloride | 4.1:1.0 |
| 2 | 1 | cupric acetate | 5.5:1.0 |
| 3 | 1 | cupric acetate | 2.5:1.0 |
| 4 | 1 | manganese (II) octoate | 10.4:1.0 |
| 5 | 1 | manganese (II) octoate | 2.7:1.0 |
| 6 | 2 | calcium sulfate | 4.2:1.0 |
| 7 | 1 | manganese (II) hydrogen phosphate | 2.9:1.0 |
| 8 | 2 | manganese (II) octoate | 9.1:1.0 |
| 9 | 2 | manganese (II) octoate | 1.9:1.0 |
| 10 | 2 | cupric chloride | 7.5:1.0 |
| 11 | 2 | cupric chloride | 3.6:1.0 |
| 12 | 2 | cupric chloride | 1.2:1.0 |
| 13 | 2 | dimethyltin (IV) | 5.8:1.0 |

TABLE II-continued

| Compound | Amine Reactant From Table 1 | Metal Salt Reactant | Mole Ratio[1] |
|---|---|---|---|
| | | dichloride | |
| 14 | 2 | stannous chloride | 5.0:1.0 |
| 15 | 2 | stannic chloride | 6.9:1.0 |
| 16 | 2 | stannous chloride & manganese (II) chloride | 6.2:1.0 1.5 |
| 17 | 2 | cupric acetate | 3.6:1.0 |
| 18 | 2 | dimethyl silicon (IV) dichloride | 2.1:1.0 |
| 19 | 2 | nickel (II) bis [(di-z ethylhexyl) acid phosphate] | 11.3:1.0 |
| 20 | 3 | cupric oleate | 6.0:1.0 |
| 21 | 3 | manganese (II) octoate | 4.4:1.0 |
| 22 | 4 | lead (II) dichloride | 6.3:1.0 |
| 23 | 4 | aluminum trichloride | 4.1:1.0 |
| 24 | 5 | cupric chloride | 7.3:1.0 |
| 25 | 6 | cupric oleate | 3.2:1.0 |
| 26 | 6 | ferric chloride | 5.1:1.0 |
| 27 | 6 | zinc phosphate | 11.8:1.0 |
| 28 | 6 | nickel (II) bis [(di-2-ethyl hexyl) acid phosphate] | 15.1:1.0 |
| 29 | 7 | cupric acetate | 2.9:1.0 |
| 30 | 7 | cupric oleate | 6.1:1.0 |
| 31 | 7 | magnesium phosphate | 10.2:1.0 |
| 32 | 8 | manganese (II) octoate | 6.1:1.0 |
| 33 | 9 | chromium acetate | 9.1:1.0 |
| 34 | 9 | manganese oleate | 9.3:1.0 |
| 35 | 10 | cupric chloride | 4.1:1.0 |
| 36 | 10 | cupric bis (2-ethyl hexyl acid phosphate) | 6.9:1.0 |
| 37 | 10 | stannous bis(2-ethyl-hexanoate) | 4.1:1.0 |
| 38 | 11 | stannous bromide | 7.1:1.0 |
| 39 | 11 | cobalt naphthenate | 8.1:1.0 |
| 40 | 11 | manganese (II) chloride | 7.2:1.0 |
| 41 | 12 | cupric acetate | 7.6:1.0 |
| 42 | 12 | zirconium (IV) bromide | 17.2:1.0 |
| 43 | 12 | manganese (II) chloride | 3.3:1.0 |
| 44 | 13 | cupric chloride | 4.4:1.0 |
| 45 | 13 | manganese (II) chloride | 4.5:1.0 |
| 46 | 13 | cuprous chloride | 4.0:1.0 |
| 47 | 14 | cupric chloride | 3.6:1.0 |
| 48 | 14 | manganese (II) octoate | 2.9:1.0 |

NOTES:
[1]Refers to mole ratio of amine to metal salt.

Finally, the metal amine complexes obtained as a result of the reactions set forth in Table II above were added to controlled amounts of asphalt cement. The resultant mixtures were then tested and analyzed after 1, 3, 5 and 10 freeze/thaw cycles using known analytical techniques to determine their relative strength characteristics under both "wet" and "dry" conditions. The results of those tests are set forth in Table III below.

TABLE III

| Table No. Compound No.[1] | Dry Tensile Strength (psi)[2] | Tensile Strength Ratio[3] | | | |
|---|---|---|---|---|---|
| | | 1 FTC[3] | 3 FTC[3] | 5 FTC[3] | 10 FTC[3] |
| I-1 | 123 | .89 | .83 | .79 | .62 |
| II-1 | 119 | 1.06 | .98 | .92 | .86 |
| II-2 | 135 | 1.09 | 1.01 | .95 | .92 |
| II-3 | 148 | 1.07 | 1.06 | 1.00 | .94 |
| II-4 | 154 | 1.14 | .84 | .75 | .65 |
| II-5 | 151 | 1.02 | .88 | .73 | .59 |
| II-6 | 133 | 1.00 | .91 | .84 | .75 |
| II-7 | 150 | 1.10 | .92 | .81 | .68 |
| I-2 | 121 | .96 | .81 | .72 | .59 |
| II-8 | 144 | 1.17 | .97 | .82 | .74 |
| II-9 | 154 | 1.05 | .82 | .71 | .55 |
| manganese (II) octoate | 141 | 0 | — | — | — |
| II-10 | 128 | 1.05 | .91 | .84 | .71 |
| II-11 | 125 | 1.10 | 1.02 | .97 | .85 |
| II-12 | 136 | .87 | .74 | .61 | .50 |
| II-13 | 133 | 1.13 | 1.08 | 0.94 | .90 |
| II-14 | 130 | 1.15 | 1.11 | 1.04 | 1.01 |
| II-15 | 118 | .87 | .72 | .65 | .52 |
| II-16 | 141 | 1.10 | .94 | .83 | .77 |
| II-17 | 139 | 1.09 | 1.02 | .94 | .90 |
| II-18 | 147 | 1.13 | 1.04 | 1.09 | 1.03 |
| II-19 | 129 | 1.02 | .94 | .86 | .77 |
| cupric oleate | 125 | 0 | — | — | — |
| I-3 | 118 | .97 | .92 | .87 | .80 |
| II-20 | 127 | 1.07 | 1.02 | .97 | .92 |
| II-21 | 149 | 1.03 | .92 | .87 | .78 |
| II-22 | 138 | 1.05 | .98 | .90 | .81 |
| I-4 | 127 | .99 | .90 | .81 | .69 |
| II-23 | 137 | 1.02 | .94 | .86 | .79 |
| II-24 | 126 | 1.12 | .97 | .92 | .82 |
| I-6 | 123 | .96 | .90 | .84 | .76 |
| II-25 | 131 | 1.08 | 1.04 | 1.04 | .94 |
| II-26 | 136 | 1.03 | .97 | .90 | .80 |
| II-27 | 129 | 1.02 | .94 | .91 | .84 |
| II-28 | 134 | 1.07 | .99 | .90 | .91 |
| II-29 | 129 | .99 | .91 | .86 | .77 |
| I-7 | 123 | .90 | .80 | .69 | .48 |
| II-30 | 124 | 1.02 | .95 | .90 | .84 |
| II-31 | 118 | .91 | .84 | .82 | .71 |
| II-32 | 130 | .90 | .81 | .72 | .61 |
| II-33 | 134 | .99 | .90 | .79 | .72 |
| II-34 | 142 | 1.09 | 1.02 | .93 | .81 |
| II-35 | 120 | 1.04 | 1.01 | .92 | .87 |
| II-36 | 132 | 1.14 | 1.09 | 1.02 | .92 |
| II-37 | 130 | 1.09 | 1.04 | 1.04 | 1.00 |
| II-38 | 129 | 1.04 | 1.00 | .97 | .90 |
| I-11 | 124 | .92 | .84 | .80 | .75 |
| II-39 | 141 | .89 | .88 | .81 | .72 |
| II-40 | 146 | 1.09 | .94 | .90 | .86 |
| I-12 | 129 | .98 | .92 | .87 | .79 |
| II-41 | 134 | 1.10 | 1.04 | .95 | .90 |
| II-42 | 131 | .89 | .80 | .71 | .60 |
| II-43 | 148 | 1.09 | .98 | .90 | .85 |
| II-44 | 128 | .91 | .91 | .82 | .79 |
| II-45 | 141 | .84 | .74 | .69 | .65 |
| II-46 | 130 | .92 | .90 | .83 | .80 |
| II-47 | 135 | 1.07 | 1.01 | .92 | .88 |

NOTES:
[1]Each additive is tested at a use level of 0.5% based upon asphalt weight
[2](a) All specimens are of the following formula: 94.5% granite gneiss aggregate 5.5% AC-20 asphalt (containing 0.5 wt % additive)
(b) Testing conducted in accordance with the indirect tensile strength measurement of asphalt concrete as described by R. P. Lottman in NCHRP Report 192.
[3](a) Tensile Strength Ratio = $\frac{\text{Tensile Strength — Wet Conditioned Specimens}}{\text{Tensile Strength — Dry Conditioned Specimens}}$
(b) FTC = Freeze-Thaw Cycles The comparative strength values set forth in Table III confirm that asphalt compositions containing the metal amine complexes produced in accordance with the present invention exhibit significant increases in overall tensile strength relative to compositions which do not contain such complexes.

In particular, the metal amine complexes of this invention have the unexpected ability to increase the dry tensile strength of asphalt compositions and to further increase the wet tensile strength over the dry strength for these asphalt compositions as compared to asphalt compositions not containing such metal amine complexes as additives. This wet strength increase is evident from Table III for the components which produce asphalt concrete compositions which have a tensile strength ratio greater than 1.0 after one freeze-thaw cycle. Further examination of Table III reveals that the metal amine complexes as additives display superior durability properties to the uncomplexed amine additives despite the lack of any wet strength improvement noted when the metals are used as additives by themselves.

It should be noted that there is considerable fluctuation in properties depending on the amine used, the metal used and the anion used. In general, stannic tetrahalide and silicon tetrahalide tend to give poorer results regardless of the amine.

While the invention herein has been shown and described in what is presently believed to be the most practical and preferred embodiment thereof, it will be apparent to those of ordinary skill in the art that many modifications may be made within the scope of the invention, which scope is to be accorded the broadest interpretation of the appended claims so as to encompass all equivalent methods and compositions. The compositions can comprise, consist essentially of or consist of the stated materials.

What is claimed is:

1. A composition of matter comprising a metal amine complex and an asphalt, said metal amine complex comprising the reaction product of an amine and a salt, wherein said amine is at least one species selected from the group consisting of:

A.

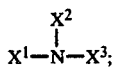   General Formula I

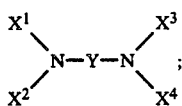   General Formula II and adducts of said amines with ethylene oxide; alkyl, cycloalkyl, or aryl-substituted ethylene oxide; or cyclohexylene oxide; wherein:

i. $X^1$, $X^2$, $X^3$, and $X^4$ are independently selected from:

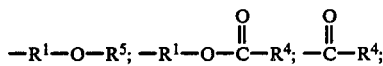

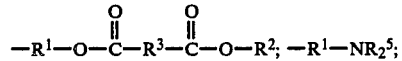

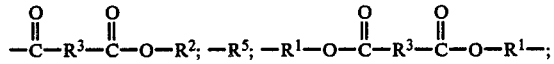

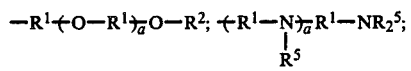

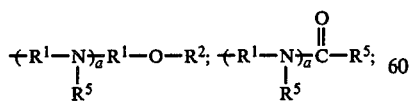

and hydrogen; or $X_1$ and $X_2$ or $X_3$ and $X_4$ together form a 5 or 6-membered ring containing at least one nitrogen atom, the ring optionally containing at least one oxygen atom or being substituted by $R^5$, provided that at least one X or one $R^5$ must be hydrogen;

ii. Y is selected from the group consisting of

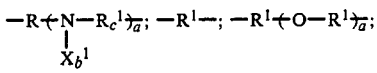

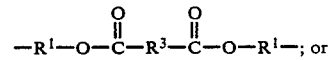

forms a six-membered ring with the two nitrogens of General Formula II;

iii. R is selected from alkylene of from one to six carbon atoms and a six-membered ring formed with two nitrogens;

iv. $R^1$ is alkylene of from 1 to 20 carbon atoms, cycloalkylene, arylene, or the previous substituted by hydroxy, ester or hydrocarbyl;

v. $R^2$ is alkyl of from 1 to 20 carbon atoms, cycloalkyl, aryl, alkaryl, aralkyl, hydrogen, or the previous substituted by hydroxy or ester;

vi. $R^3$ is alkylene, cycloalkylene, arylene, or the previous substituted by hydrocarbyl, hydroxyl, ester; or alternatively $R^3$ is

vii. $R^4$ is alkenyl of from 1 to 20 carbon atoms, alkyl, aryl, alkaryl, aralkyl, or cycloalkyl, optionally substituted by hydroxy or ester;

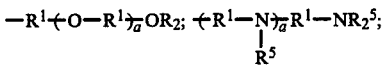

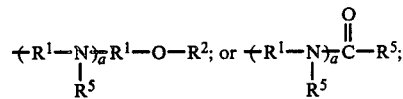

viii. $R^5$ is hydrogen; alkenyl, alkyl, cycloalkyl, aryl, alkaryl, aralkyl, or the previous substituted by hydroxy, ester, alkyl imidazoline or alkenyl imidazoline; alkyl imidazoline, alkenyl imidazoline,

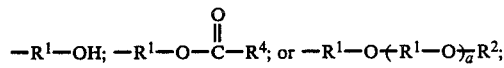

ix. a is 0 or 1; b is 0, 1, or 2; c is 0, 1, or 2; and x. compounds which contain at least two nitrogen atoms are not within the scope of General Formula I if they fall within the scope of General Formula II;

B. a reaction product of A and a formaldehyde source;

C. a reaction product of B and an oxirane selected from alkyl, cycloalkyl, aryl, or cycloalkylene oxiranes;

D. a reaction product of A and an oxirane selected from cycloalkyl, aryl, alkyl, or cycloalkylene oxiranes; and E. a reaction product of D and a formaldehyde source; and wherein said salt comprises:

F. at least one cation selected from metals of Groups II A, IV B, VI B (except molybdenum), VII B, VIII, I B, II B, III A, or IV A of the Periodic Table; mono- or dialkyltin; and mono-, di-, or trialkylsilicon; and G. at least one anion selected from the group consisting of chloride, bromide, oxide, hydroxide, sulfate, formate, acetate, carboxylate of formula:

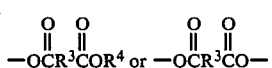

and derivatives of phosphoric and phosphorous acids.

2. The composition of claim 1, wherein said amine is as defined in part A.

3. The composition of claim 1, wherein said amine is as defined in part B.

4. The composition of claim 1, wherein said amine is as defined in part C.

5. The composition of claim 1, wherein said amine is as defined in part D.

6. The composition of claim 1, wherein said amine is as defined in part E.

7. The composition of claim 1, wherein said at least one cation is one of said metals.

8. The composition of claim 1, wherein said at least one cation is selected from monoalkyltin, dialkyltin, monoalkylsilicon, dialkylsilicon, and trialkylsilicon.

9. The composition of claim 1, wherein if the said amine is of General Formula I it has at least one amino nitrogen atoms and if the said amine is of General Formula II, any alkyl group attached to an amino nitrogen is methyl.

10. A composition according to claim 1 wherein said cation is copper; tin; mono- or dialkyltin; mono-, di- or trialkylsilicon; or manganese.

11. The composition according to claim 1 wherein the metal is tin or silicon and the anion is not tetrahalide.

12. The composition of claim 1 wherein said amine conforms to the general formula:

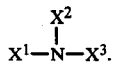

13. A composition of claim 1 wherein said amine conforms to the general formula:

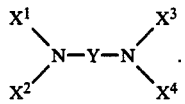

14. The composition of claim 1 wherein said amine possesses at least one X which is $-R^1-O-R^5$.

15. The composition of claim 2 wherein said amine possesses at least one X which is:

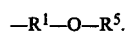

16. The composition of claim 1 wherein said amine possesses at least one X which is:

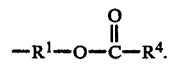

17. The composition of claim 1 wherein said amine possesses at least one X which is:

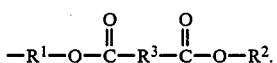

18. The composition of claim 1 wherein said amine possesses at least one X which is:

$-R^1-NR_2^5$.

19. The composition of claim 1 wherein said amine possesses at least one X which is:

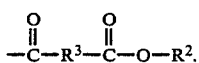

20. The composition of claim 1 wherein said amine possesses at least one X which is:

$-R^5$.

21. The composition of claim 1 wherein said amine possesses at least one X which is:

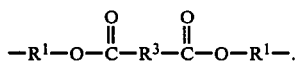

22. The composition of claim 1 wherein said amine possesses at least one X which is

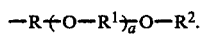

23. The composition of claim 1 wherein said amine possesses at least one X which is:

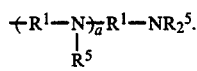

24. The composition of claim 1 wherein said amine possesses at least one X which is

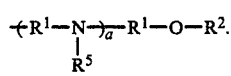

25. The composition of claim 1 wherein said amine possesses at least one X which is:

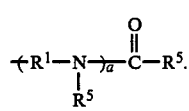

26. The composition of claim 1 wherein said amine possesses at least one X which is hydrogen.

27. The composition of claim 1 wherein said amine possesses one Y which is:

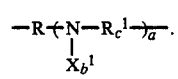

28. The composition of claim 1 wherein said amine possesses one Y which is:

$-R^1-$.

29. The composition of claim 1 wherein said amine possesses one Y which is:

$-R^1+OR^1\overline{)_a}-$.

30. The composition of claim 1 wherein said amine possesses one Y which is:

31. A composition of claim 1 wherein said amine possesses one Y which forms a six-membered ring containing two nitrogens.

32. The composition of claim 1 wherein said amine possesses at least one X which forms a 5 or 6-membered ring containing at least one nitrogen atom and carbon atoms with or without oxygen atoms and can be substituted by $R^5$.

33. A composition according to claim 1, further comprising a filler selected from mineral aggregate, glass fibers, and glass fiber mesh.

34. A composition according to claim 33 wherein the filler comprises mineral aggregate, the amount of said complex being sufficient to impart improved tensile strength properties to the composition of asphalt and aggregate.

35. A composition according to claim 33 wherein the filler comprises glass fibers.

36. A composition according to claim 33 wherein the filler comprises a glass fiber mesh.

37. A method of increasing the tensile strength of an asphalt coated filler, comprising the steps of:
   A. providing a composition according to claim 1 and a filler selected from mineral aggregate, glass fibers, and glass fiber mesh; and
   B. coating said filler with said composition.

38. The method of claim 33, wherein said filler is a mineral aggregate.

39. The method of claim 37, wherein said filler is glass fiber mesh.

40. The method of claim 37, wherein said filler is glass fiber.

41. The composition of claim 1, wherein said metal amine complex has the structure of General Formula II and is free of alkyl groups attached to any amino nitrogen atom.

42. The product of the process of claim 37.

* * * * *